United States Patent
Meyers

(10) Patent No.: US 9,177,462 B1
(45) Date of Patent: Nov. 3, 2015

(54) RISK PROFILING USING PORTAL BASED SCANNERS

(75) Inventor: Richard C. Meyers, Longboat Key, FL (US)

(73) Assignee: GlobalTrak, LLC, Sterling, VA (US)

( * ) Notice: Subject to any disclaimer, the term of this patent is extended or adjusted under 35 U.S.C. 154(b) by 194 days.

(21) Appl. No.: 13/310,769

(22) Filed: Dec. 4, 2011

Related U.S. Application Data

(60) Provisional application No. 61/420,244, filed on Dec. 6, 2010.

(51) Int. Cl.
*G08B 29/00* (2006.01)
*G08B 23/00* (2006.01)
*G06Q 10/08* (2012.01)
*G08B 25/14* (2006.01)

(52) U.S. Cl.
CPC ............... *G08B 23/00* (2013.01); *G06Q 10/08* (2013.01); *G08B 25/14* (2013.01)

(58) Field of Classification Search
CPC ........ G08B 23/00; G08B 25/14; G08B 25/00; G06Q 10/08; G06Q 10/087; G06Q 10/0833; G06Q 20/203

USPC .......... 340/500, 539.1, 539.13, 545.1, 545.6, 340/10.1, 10.3, 572.1–572.9; 455/41.2; 235/385, 384, 375
See application file for complete search history.

(56) References Cited

U.S. PATENT DOCUMENTS

| | | | |
|---|---|---|---|
| 7,098,784 B2 * | 8/2006 | Easley et al. | 340/539.13 |
| 7,200,132 B2 * | 4/2007 | Twitchell, Jr. | 370/338 |
| 7,339,469 B2 * | 3/2008 | Braun | 340/539.13 |
| 7,991,357 B2 * | 8/2011 | Meyers et al. | 455/41.2 |
| 2009/0322510 A1 * | 12/2009 | Berger et al. | 340/539.1 |

* cited by examiner

*Primary Examiner* — Anh V La

(57) ABSTRACT

A system and method for consolidating data collected using a hierarchical scanning system and assessing security risks regarding the shipping containers is provided. The hierarchical scanning system collects information from distributed and repeated screening throughout a container journey and enables pattern analysis over groups of containers. During the journey of a container, risk profiles are created at short term events based on information collected via non-intrusive rapid inspections. Using combined information from the risk profiles, the initial manifest, and group based statistical intelligence, a risk quotient for each container is determined based on deviations calculated at each point of the journey. Accordingly, authorities are alerted when the risk quotient indicates that a specific container is at risk.

6 Claims, 3 Drawing Sheets

RISK PROFILING USING PORTAL BASED SCANNERS

PRIORITY CLAIM

The present invention claims U.S. Provisional Application No. 61/420,244, filed Dec. 6, 2010. No new matter has been claimed.

BACKGROUND OF THE PRESENT INVENTION

1. Field of the Present Invention

The present invention relates generally to using detection technology to quickly pre-screen containers to identify containers that pose a risk to U.S. security. More particularly, the present invention relates to a hierarchical scanning system with long term/short term events, a profiler, and data analysis to find patterns related to groups of containers derived from non-intrusive and rapid inspection techniques for a shipping container monitoring system.

2. Description of Related Art

The Container Security Initiative (CSI) was launched in 2002 by the U.S. Bureau of Customs and Border Protection (CBP), an agency of the Department of Homeland Security. Its purpose was to increase security for container cargo shipped to the United States.

Containerized shipping is a critical component of international trade. About 90% of the world's trade is transported in cargo containers and almost half of incoming U.S. trade (by value) arrives by containers on-board ships. Nearly seven million cargo containers arrive on ships and are off-loaded at U.S. seaports each year.

As terrorist organizations have increasingly turned to destroying economic infrastructure to make an impact on nations, the vulnerability of international shipping has come under scrutiny. Under the CSI program, the screening of containers that pose a risk for terrorism is accomplished by teams of CBP officials deployed to work in concert with their host nation counterparts.

CSI consists of four core elements: using intelligence and automated information to identify and target containers that pose a risk for terrorism; pre-screening those containers that pose a risk at the port of departure before they arrive at U.S. ports; using detection technology to quickly pre-screen containers that pose a risk and using smarter, tamper-evident containers.

These four elements of the CSI recognize that container security may be compromised at many stages in the transit of a container. Ideally, the goal would be for each container to be pre-screened during each transitional event a container undergoes (i.e. from a ship onto a dock, from a dock into the storage yard, from the storage yard onto the bed of a truck, from the bed of a truck into another storage yard, and from the storage yard lifted onto another ship. Long term events, which are defined here as events lasting for several hours to several weeks, pose a greater likelihood that a tampering episodes may occur. At the same time, each short term event which usually involves a container transfer is an opportune time to scan containers. Thus, repeated screening of containers and verifying container condition and contents will ensure the highest possible confidence that a container is secure.

SUMMARY OF THE PRESENT INVENTION

The present invention recognizes that the screening process must occur over and over again at all points in the journey of a container. It also recognizes that there are some transitional events such as the off-loading of a container from a ship or passage through a security checkpoint that are going to be short term events, while other events like storage or travel will be long term events. The nature and level of detail which can be scanned and collected will differ significantly based on the duration of each transitional event. According to a preferred embodiment of the present invention, based on quick interactions events (loading and unloading), a profile may be created which will prioritize containers for inspection during longer term events such as storage.

To obtain such data, the present invention uses a non-intrusive and rapid inspection technique for short term interaction with a shipping container. More specifically, sensors placed on cranes or other devices which interact with containers will collect and transmit data to a central monitoring station or "data fusion center." Data gathering would create a risk profile during container transit. Deviations in the data from checkpoint to checkpoint would be used to pinpoint and prioritize which specific containers should undergo a complete inspection. The accompanying drawings, which are incorporated in and constitute part of the specification, illustrate various embodiments of the present invention and together with the description, serve to explain the principles of the present invention.

DESCRIPTION OF THE PREFERRED EMBODIMENTS

Figure 1:
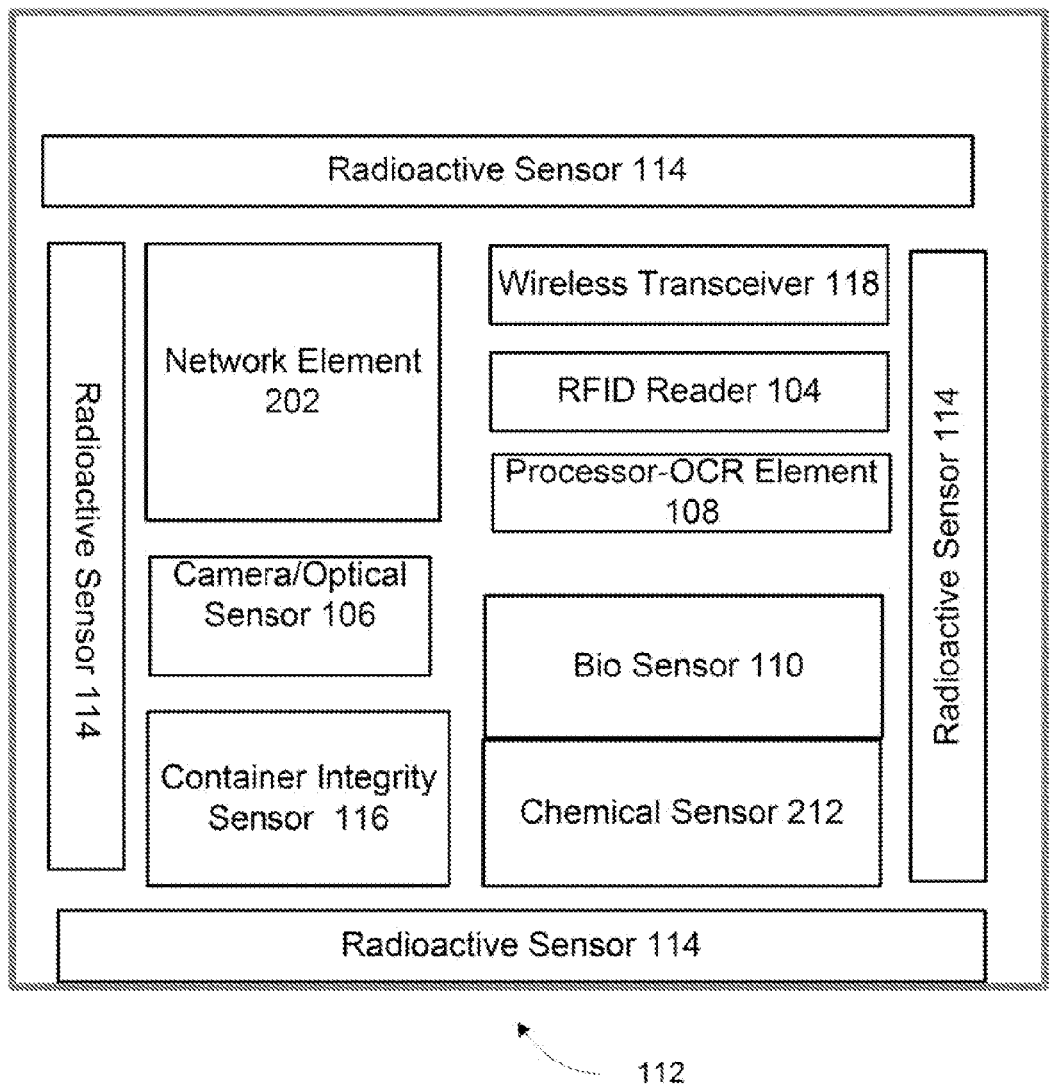
FIG. 1 shows a block diagram of the components of a portal based scanner in accordance with an embodiment of the present invention.

For the purposes of promoting an understanding of the principles of the present invention, reference will now be made to the embodiments illustrated in the drawings and specific language will be used to describe the same. It will nevertheless be understood that no limitation of the scope of the present invention is hereby intended and such alterations and further modifications in the illustrated devices are contemplated as would normally occur to one skilled in the art.

The terms "program," "computer program," "software application," and the like as used herein, are defined as a sequence of instructions designed for execution on a computer system. A program, computer program, or software application may include a subroutine, a function, a procedure, an object implementation, an executable application, an applet, a servlet, a source code, an object code, a shared library, a dynamic load library and/or other sequence of instructions designed for execution on a computer system. A data storage means, as defined herein, includes many different types of computer readable media that allow a computer to read data therefrom and that maintain the data stored for the computer to be able to read the data again. Such data storage means can include, for example, non-volatile memory, such as ROM, Flash memory, battery backed-up RAM, Disk drive memory, CD-ROM, DVD, and other permanent storage media. However, even volatile storage such a RAM, buffers, cache memory, and network circuits are contemplated to serve as such data storage means according to different embodiments of the present invention.

All dimensions as shown in the figures and described in the specification have been selected to simplify explanations. However, it is understood that there are many variables in the sizes and dimensions of cargo containers, cranes assemblies, transport vehicles, storage areas and loading docks that must be taken into consideration by one skilled in the art when adapting the present invention.

With reference now to FIG. 1, a block diagram of the components of a portal based scanner in accordance with an embodiment of the present invention is provided. An example portal based scanner is described in detail in the Provisional Application by the same inventor entitled "Apparatus for Portal Based Scanner" which is hereby incorporated by reference. As shown in FIG. 1, a portal based scanner 112 preferably includes: a plurality of sensors and a network element 202 which are communicatively coupled via cabling; and a wireless communication link via wireless transceiver 118. As shown, the exemplary sensor suite of the portal based scanner 112 further includes: a RFID reader 104; a processor-OCR element 108; a camera/optical sensor 106; a container integrity sensor 116; a bio sensor 110; a chemical sensor 212; and an array of radioactive isotope sensors 114. The radioactive isotope sensors 114 may detect gamma radiation and/or neutrons. The Container Integrity Sensor 116 may be an infrared spectroscopic sensor and/or a passive ultrasonic sensor. The Bio Sensors 110 and Chemical Sensors 212 may be optical chemical/biosensor, optical, electrochemical, piezoelectric, and/or volt metric sensors.

The network element 202 includes a data collecting system and an information processing system with data communication interfaces that collect signals from the sensor units. The collected signals represent detailed data from each sensor device. A user interface allows remotely located service or supervisory personnel to operate the local system and to monitor the status of the shipping container via the collection of sensor units deployed on a portal based scanner.

The portal based scanners of the present invention may be configured into one or more panels which may be positioned to create specific areas of focus for scanning. Further, according to a further aspect of the present invention, the portal based scanners are preferably configured to interrogate containers to determine whether a container is a smart container or not. If container is a smart container, then processing systems and interfacing units will further interrogate sensors within structural integrity of the container to quickly identify and assess sensor status. If container makes no response when interrogated, portal based scanner will assume the container is not actively monitored (i.e. "dumb") and it will identify the container via optical sensors 106 and assess the condition of container via container integrity sensor 116. Also preferably, the portal based scanners can be manually and/or automatically programmed to adjust the settings of the length of the operation of the scanner based on how much time a specific interaction event with the container takes and the size of the container.

The present invention may be mounted to fit a plurality of pieces of equipment such as but not limited to a Rail Mounted Gantry Crane, a hook crane, a slewing/luffing crane, a magnetic crane, transport vehicles, security checkpoints, and entrances and exits in storage yards. Accordingly to one aspect of the present invention, the portal based scanners may be deployed when the spreader bar is fully engaged. According to this aspect, the scanners are preferably configured to perform a 30-40 second scan of the length of the container thereby completing a close proximity non-intrusive scan which creates or updates a risk profile for the container 108. Preferably, there are at least two portal based scanners employed to scan each container and in some embodiments depending on the amount of time and the size of the containers, more than two portal based scanners may be necessary.

Figure 2:
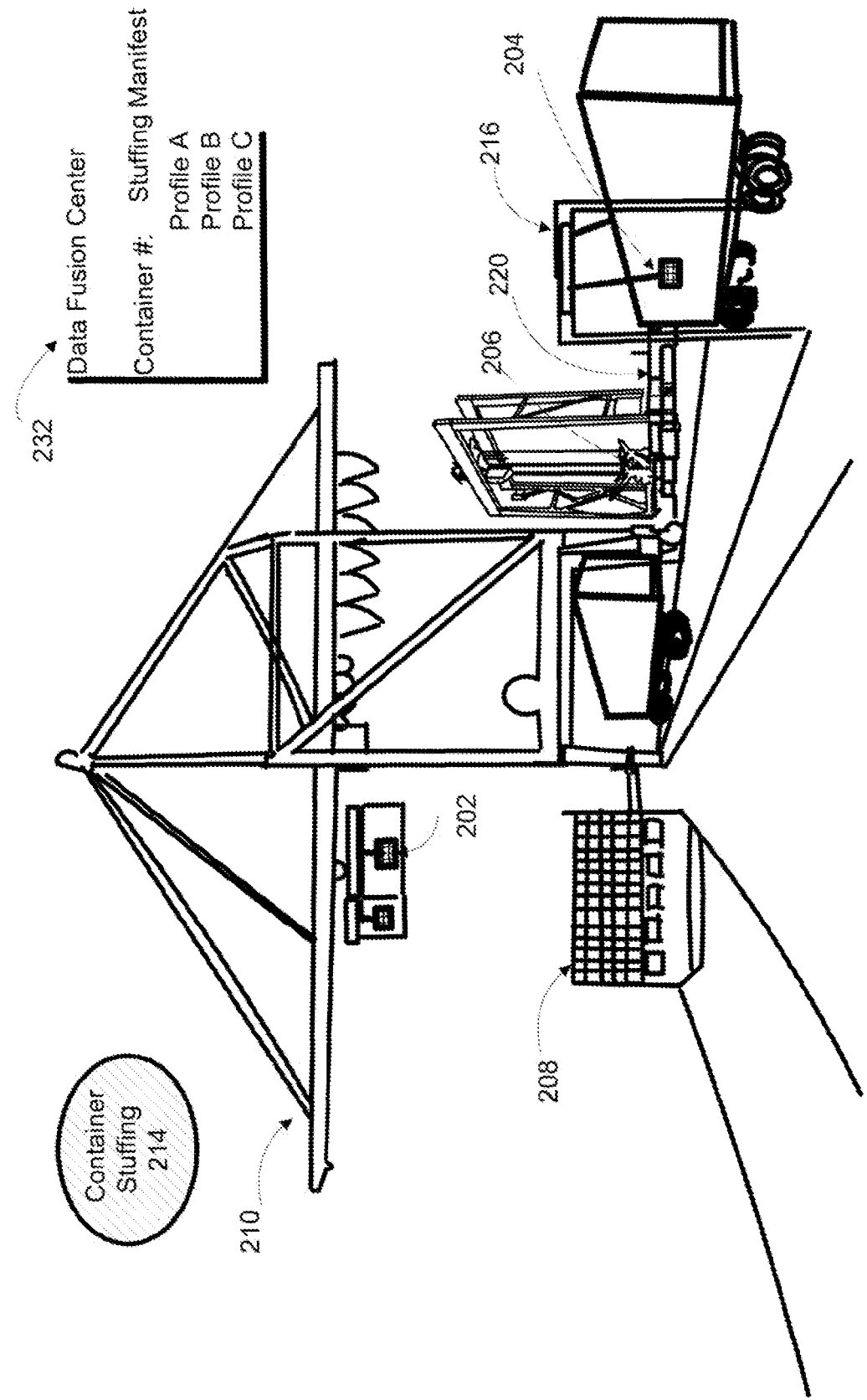
FIG. 2 shows a functional configuration of an exemplary placement of scanners associated with an inspection system in accordance with an embodiment of the present invention.

With reference now to FIG. 2, a functional configuration of an exemplary placement of scanners associated with an inspection system in accordance with an embodiment of the present invention will now be discussed. As shown in FIG. 2, there are three long term events (several hours to weeks) which cargo containers which may be subject to: stuffing 214, travelling 208, and storage 320. The container stuffing 214 is the first long term event from which the initial manifests and inventories are completed and transmitted to the Data Fusion Center 232. Preferably, an initial scan of the container by a portal based scanner 202 will occur as container is initially uploaded onto the ship 208 by the dockside gantry crane 210 and this initial short term interaction with cargo container will produce a Profile A.

Profile A may include sensor information about chemical residue, bio residue, the presence of radioactive isotopes, a picture of identifying numbers, and an image of the container's overall condition and integrity. Profile A will establish initial threshold data pertaining to these sensors with data checked to ensure that results fall into acceptable ranges. Therefore, subsequent short term interactions with the cargo container will gather additional information to form additional risk profiles pertaining to a container. If at any point in the gathering of data, a container risk profile is changed or distorted, then it is flagged and the inspecting authorities are alerted to inspect the container.

As shown in FIG. 2, the portal based scanner 206 additionally gathers data about each container in a short term interaction as it transfers and stacks containers in the storage yard 220 and the data collected is transmitted to the Data Fusion Center 232 where a risk profile is created and compared to other profiles pertaining to a specific container.

As further shown in FIG. 2, a portal based scanner 204 may be secured and retractably attached to the structural frame of the security gate 216 of the storage yard. In this arrangement, the portal based scanner 204 interrogates and collects data about each container that enters the storage yard and transmits the data to the Data Fusion Center 232 where a risk profile is created and compared to the manifest and other risk profiles for that specific container. Any deviation in scanner test results for a given container increases the risk quotient which will identify a container for inspection. Preferably, port authorities or other inspecting authorities are alerted by the risk quotient variation associated with a specific container and the "at risk" container may be scheduled for complete inspection either within the storage yard area or another area where authorities are operating.

Figure 3:
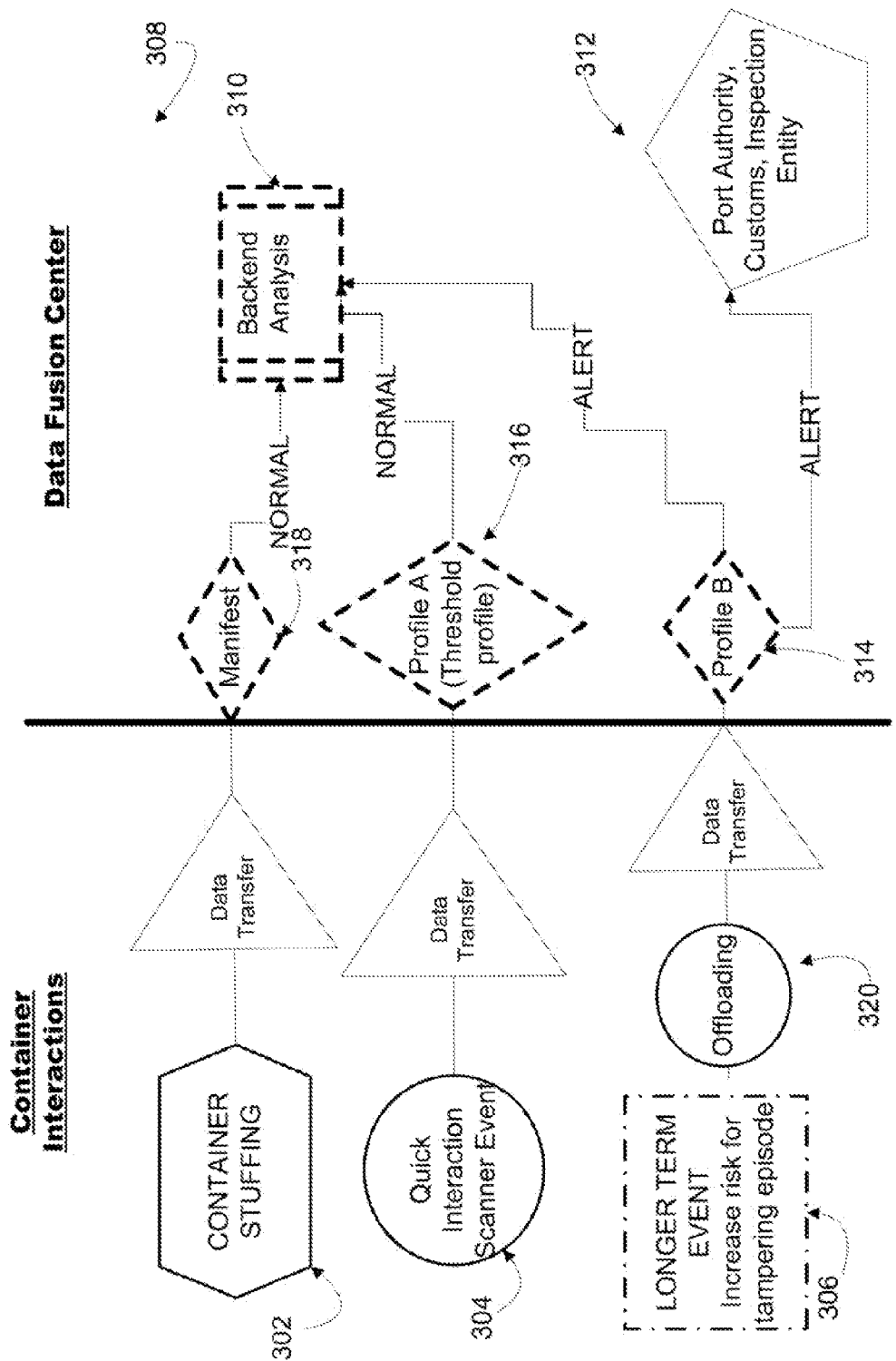
FIG. 3 shows a flow chart diagram of the hierarchical scanning system in accordance with an embodiment of the present invention.

With reference now to FIG. 3, a flow chart diagram of the hierarchical scanning system in accordance with an embodiment of the present invention is provided. As shown in FIG. 3, when a container is stuffed 302 data is transferred to the Data Fusion Center 308 in the form of an initial manifest 318. The initial manifest 318 may include any identifying information about the container such as inventory lists, the container itinerary and shipping and contact information. A quick interaction scanner event 304 happens when the container is loaded onto a ship. The portal based scanner transmits scanner data to the Data Fusion Center 308 which produces Profile A 316 in which normal sensor ranges provide a baseline to which subsequent risk profiles may be compared. A Longer Term Event 306, such as travel time on a ship, which can last from several hours to several weeks exposes a container to an increased risk of a tampering episode. Hence, when the container is involved in a short term interaction with a portal based scanner during it's next offloading 320 and data is transferred to the Data Fusion Center 308, Profile B 314 is created and compared to earlier profiles. In this process, data is analyzed to determine if any parameter is outside of an acceptable range. If so, this triggers an alert which is communicated directly to the inspection authorities 312. This alert may be used to prioritize the container for immediate inspection.

As further shown in FIG. 3, Backend Analysis 310 at the Data Fusion Center 308 preferably analyzes profile patterns that are impacting how inspections are sampled. Container Risk Profiles may be used to compare, for example, profiles from containers that have be shipped by the same company, profiles from containers that were loaded in a particular storage yard or profiles from containers due to arrive at the same ports of entry. The statistical intelligence derived from this kind of analysis can be used to determine inspection priorities based on extrapolating information about recurring times and places where risk is found to be increased.

Communication System

In accordance with a preferred embodiment of the present invention, the reporting may be made via a wireless connection to a satellite mode to communicate with a satellite system such as Globalstar or Orbcomm. Preferably, such a satellite device will be a device such as the Axxon, AutoTracker, or the like, or a customized Orbcomm VHF satellite GPS tracking communications device which may be adapted with Zigbee interface antenna devices to incorporate them into the overall LAN architecture of the security system; these devices include a satellite transceiver, GPS receiver, a customized Zigbee wireless antenna with a serial (Ax Tracker) or duplex (OrbComm) interface.

In accordance with an alternative preferred embodiment of the present invention, the reporting may also be made using a wireless system independent from the satellite system. According to this embodiment, wireless signals may be transmitted to a wireless relay, base station or the like for routing and transmission to a chosen centralized location independent from or in combination with the transmissions made from the satellite system. In accordance with this alternative embodiment, signals may also be received by the communications manager and wireless interface from such external wireless networks as well.

According to a preferred embodiment of the present invention, it is preferred that the wireless communications used within the present invention will be based on the Zigbee (IEEE 802.15.4) standard. This standard transmits RF signals in the 2.4 GHz ISM band and operates with low power consumption due to its relatively slower data transmission rate (128 Kpps-250 Kbps). This approach enables additional capacity and flexibility of design through an up to 255 node pico-network. Communications are simplex or duplex in design, meaning that data can be assessed in either a push or pull process.

As referred to above, all communications of the present invention may be designed to be duplex or simplex in nature. Further, as needs require, the processes for transmitting data to and from the present invention may be designed to be push or pull in nature. Still, further, each feature of the present invention may be made to be remotely activated and accessed from distant monitoring stations. Accordingly, data may preferably be uploaded to and downloaded from present invention as needed. For example, as detailed above, each system and subsystem of the present invention may be designed to send, receive, report and request information via the wireless and/or satellite systems so as to continually maintain and update the container systems.

Additional communications with the communications manager are preferably enabled via industry standard wired interfaces, with communications protocols implemented in firmware for future upgrade. These interfaces preferably will include at least two RS-322 compatible serial ports. These alternate serial ports may assist the communications manager to interface with additional remote sensors as well as other local reader/controllers such as an RFID reader or other devices.

Remote Monitoring

To support and monitor the dataflow generated by the present invention, it is preferred that users establish a centralized location to collect and analyze data. This central location or "data fusion center" would preferably consolidate all tracking signals, sensor alarms and reports generated by the monitoring systems and provide further context and links with current intelligence.

Preferably, such a data fusion center will receive such source information in a variety of formats such as Electronic Data Interchange, XML, E-mail, HTML and flat text files. After receiving such data, the data fusion center preferably would act to process information to identify anomalies. With this data collected and processed, analyst may calculate statistics and probability of detection models used for decision support.

In terms of decision making, such a data fusion center would assist agents and shippers in making decisions regarding the safety and status of each container. In short, such a data fusion center would preferably provide a consolidated source of information that could be used to assist agencies and shippers to identify and remove unsafe and suspicious containers from commerce.

What is claimed is:

1. A scanning system for monitoring shipping containers during transport, the system comprising:
    a portal based scanner configured to directly detect one or more exterior characteristics of a transported shipping container; wherein the portal based scanner is attached to structures or equipment which handle shipping containers during short term events;
    a data fusion center that collects and consolidates information from a plurality of portal based scanners;
    a first communication element that provides information exchange between the portal based scanner and the data fusion center, wherein the portal based scanner gathers data about at least one container in a short term interaction and transmits the data to the data fusion center;
    a processing element for identifying anomalies based on the detected exterior characteristics of the transported shipping container and for
    generating an alert according to identified anomalies.

2. The system of claim 1, wherein the data fusion center creates a risk profile for at least one container based on the one or more exterior characteristics detected during the short term event.

3. The system of claim 2, wherein the processing element compares the risk profile to at least one risk profile from a previous short term interaction and identifies any anomalies.

4. The system of claim 1, further comprising a backend analysis module that analyzes patterns among a group of shipping containers and generates statistical intelligence.

5. The system of claim 1, wherein the data fusion center consolidates multiple sources of information and alarms to assist agencies to identify suspicious containers.

6. The system of claim 2, wherein the risk profile comprises at least one detected characteristic from the following group:
- chemical residue;
- bio residue;
- the presence of radioactive isotopes;
- a picture of identifying numbers; and
- an image of the container's overall condition and integrity.

* * * * *